United States Patent [19]
Hirschfeld

[11] Patent Number: 4,929,561
[45] Date of Patent: May 29, 1990

[54] ABSORPTION-EMISSION OPTRODE AND METHODS OF USE THEREOF

[75] Inventor: Tomas B. Hirschfeld, Livermore, Calif.

[73] Assignee: Regents of the University of California, Oakland, Calif.

[21] Appl. No.: 763,557

[22] Filed: Aug. 8, 1985

[51] Int. Cl.$^5$ .................... G01N 21/64; G01N 21/65
[52] U.S. Cl. .................. 436/116; 250/459.1; 422/56; 422/57; 422/82.06; 422/82.07; 436/74; 436/79; 436/121; 436/172
[58] Field of Search ............... 250/373, 458.1, 459.1, 250/461.1; 436/74, 116-118, 121, 172, 537, 800, 79; 435/808; 422/55-58, 68

[56] References Cited

U.S. PATENT DOCUMENTS

| | | | |
|---|---|---|---|
| 3,904,373 | 9/1975 | Harper | 422/57 |
| 3,998,591 | 12/1976 | Eckfeldt | 422/68 |
| 4,003,707 | 1/1977 | Lubbers et al. | 436/172 |
| 4,075,493 | 2/1978 | Wickersheim . | |
| 4,132,527 | 1/1979 | Mackawa et al. | 422/56 X |
| 4,174,384 | 11/1979 | Ullman et al. . | |
| 4,200,110 | 4/1980 | Peterson et al. . | |
| 4,215,275 | 7/1980 | Wickersheim . | |
| 4,220,450 | 9/1980 | Maggio . | |
| 4,245,507 | 1/1981 | Samulski . | |
| 4,279,773 | 7/1981 | Franey et al. | 422/56 X |
| 4,344,438 | 8/1982 | Schultz . | |
| 4,447,546 | 5/1984 | Hirschfeld . | |
| 4,495,293 | 1/1985 | Shaffar | 436/172 |
| 4,682,895 | 7/1987 | Costello | 422/68 X |
| 4,724,217 | 2/1988 | Miller | 436/172 X |

FOREIGN PATENT DOCUMENTS 0072627 2/1983 European Pat. Off. .

OTHER PUBLICATIONS

Saltzman, Anal. Chem., vol. 26, No. 12, pp. 1948-1955, 12/1954.
Nakamura et al, Talanta, vol. 26, pp. 921-927, 1979.
Pacey et al, Analyst, vol. 106, pp. 636-640, 1981.
Wickersheim et al, Industrial Research & Development, "Recent Advances in Optical Temperature Measurement", 1979.
Hirschfeld, "Reabsorption Sensing in Fluorescence Spectroscopy", UCRL Abstract No. 89736 ABST, published by Pittsberg Conference on Scientific Instrumentation, 1984.

Primary Examiner—Robert J. Hill, Jr.
Attorney, Agent, or Firm—Stephen C. Macevicz; Henry P. Sartorio

[57] ABSTRACT

A method and apparatus for monitoring the physical and chemical properties of a sample fluid by measuring an optical signal generated by a fluorescent substance and modulated by an absorber substance. The emission band of the fluorescent substance overlaps the absorption band of the absorber substance, and the degree of overlap is dependent on the physical and chemical properties of the sample fluid. The fluorescent substance and absorber substance are immobilized on a substrate so that an effective number of molecules thereof are sufficiently close for resonant energy transfer to occur, thereby providing highly efficient modulation of the fluorescent emissions of the fluorescent substance by the absorber substance.

39 Claims, 3 Drawing Sheets

ABSORPTION-EMISSION OPTRODE AND METHODS OF USE THEREOF

The United States Government has rights in this invention pursuant to Contract No. W-7405-ENG-48 between the U.S. Department of Energy and the University of California, for the operation of Lawrence Livermore National Laboratory.

BACKGROUND OF THE INVENTION

The invention relates to optical means for remotely monitoring physical and chemical parameters, and particularly for generating an optical signal based on colorimetric modulation of induced fluorescence.

The utility of optically based sensors over electrically based sensors for measuring physical and chemical parameters in harsh or inaccessible environments is well established, particularly when fluorometric sensors are coupled with fiber optics, Hirschfeld, "Remote Fiber Fluorometric Analysis," *Energy and Technology Review*, pgs. 17-21 (July 1980); Seitz, "Chemical Sensors Based on Fiber Optics," *Analytical Chemistry*, Vol. 56, pgs. 16(a)-34(a) (January 1984); Peterson and Vurek, "Fiber Optic Sensors for Biomedical Applications," *Science*, Vol. 224, pgs. 123-129 (Apr. 13, 1984); and Wickersheim and Alves, "Recent Advances in Optical Temperature Measurement," *Industrial Research and Development* (December 1979). Fiber optics are durable, corrosion-resistant, heat-resistant, and impervious to electrical or magnetic interference, and are available in very small diameters, which makes them amenable for use with miniature probes. Moreover, fluorometric probes are ideally suited for use with single fibers, wherein the same fiber is used to excite the fluorometric probe and to collect the emitted fluorescence. Single fibers can be used with fluorometric probes because the difference in wavelengths between the excitation beam and the fluorescence signal allows for ready separation of the signal from the beam even though they traverse the same fiber optic at the same time. While fluorometric probes are preferred over colorimetric probes for the foregoing reason, the number of reported colorimetric probes greatly exceeds that of fluorometric, e.g., Bishop, *Indicators* (Pergammon Press, New York, 1972). The lack of a wide selection of fluorometric probes can be a stumbling block for any particular use. Not only are fluorescent probes often not available to start with, but those that are available often fail to meet needed requirements, such as nontoxicity, chemical inertness, or thermal or photochemical stability.

Shaffar, in U.S. Pat. No. 4,495,293, "Fluorometric Assay," issued Jan. 22, 1985, discloses a chemical assay method comprising a reagent system including a fluorescent agent and a chromogenic agent, such that the emission band of the fluorescent agent overlaps the absorption band of the chromogenic reagent. The chromogenic agent is further selected so that its absorption characteristics are responsive to some sample molecule of interest, in that the degree of absorption by the chromogenic agent of fluorescence emitted by the fluorescent agent is related to the concentration of the sample molecule. The assay takes place in a liquid state so that fluorescent decay occurs both by radiative and by nonradiative mechanisms. For nonradiative mechanisms to become appreciable the concentration of the chromogenic molecule must be at least $2 \times 10^{-3}$ molar (Parker, *Photoluminescence of Solutions*, Elsevier Publishing Company, New York, 1968, pgs. 83-85). At this concentration and above, many chromogenic molecules become opaque to the emissions of the fluorescent agents. Thus, for these chromogenic agents lower concentrations must be used which means that radiative decay of the excited states of the fluorescent molecules dominates, and less efficient absorption occurs. Shaffar's assay method also requires that the fluorescent agent be in direct chemical contact with the sample substance. Possible interaction between the sample substance and the fluorescent reagent greatly complicates the analysis of the optical signal generated by the assay procedure.

Energy transfer is employed in a class of immunoassay techniques which roughly are fluorescent analogs to radioimmunoassay. The techniques are exemplified by Maggio, U.S. Pat. No. 4,220,450, issued 2 Sept. 1980, entitled "Chemically Induced Fluorescence Immunoassay"; and Ullman et al., U.S. Pat. No. 4,174,384, issued 13 Nov. 1979, entitled "Fluorescence Quenching with Immunological Pairs in Immunoassays." Generally, the techniques include a stationary phase, e.g., a receptor which preferentially binds a particular ligand (the ligand being the compound whose concentration is to be determined) and a mobile phase, e.g., a ligand analog which competes with the ligand for binding sites on the receptor. A member of a fluorescer-quencher pair is covalently attached to the receptor, and the other member of the pair is covalently attached to the ligand analog. If the members of the fluorescer-quencher pair are within energy transfer distance of one another any fluorescence generated by the fluorescer is quenched. Thus, the amount of fluorescence emitted by a given number of fluorescer-labeled receptors is proportional to the number of binding sites occupied by ligand molecules relative to quencher-labeled ligand analogs. Conditions are established so that each quencher molecule reduces or quenches the fluorescence of a fluorescer molecule by the same amount.

The foregoing illustrates the limitations of the current sensor technology based on the interaction between fluorogenic and chromogenic substances. An alternative to available sensing methods which overcame some of these limitations would be highly advantageous, particularly for applications requiring monitoring of inaccessible, remote or hostile environments.

SUMMARY OF THE INVENTION

The invention is a method and apparatus for monitoring physical and chemical parameters of an associated sample substance. A substrate is provided for immobilizing a fluorescent substance and an absorber substance (the latter also being referred to as "chromogenic agent" or "chromogenic substance"). The substrate is selected so that the absorber substance can be immobilized at high surface density while maintaining low volumetric concentration. High surface density permits low average intermolecular distances between fluorescent molecules and absorber molecules so that excited fluorescent molecules are capable of decaying by resonant energy transfer to the absorber molecules. Low volumetric concentration of absorber molecules avoids the problem of opacity. An effective number of molecules of the fluorescent substance are immobilized on or in, the substrate; that is, a sufficient number of fluorescent molecules are immobilized such that a detectable fluorescent signal is generated absent the effects of the absorber molecules. Similarly, an effective number of absorber molecules are immobilized on the substrate; that is, a sufficient number of absorber molecules are within resonant energy transfer distance of a sufficient number of fluorescent molecules so that detectable modulation of radiative fluorescent decay occurs. Hereinafter, molecules within resonant energy transfer distance are referred to as being closely adjacent. Typically, the range over which resonant energy transfer takes place is between about 10–100 Angstroms, and more preferably between about 10–70 Angstroms. An important feature of the invention is that the degree of overlap between the absorption band of the absorber substance and the emission band of the fluorescent substance be responsive to the physical and chemical parameters of the sample substance, in that changes in such parameters cause correlated shifting of the spectrum of either the absorption band of the absorber substance or the emission band of the fluorescent substance or both. In most cases the shift would preferably take place in the absorption band of the absorber substance.

The invention is operated by placing the substrate in contact with the sample substance, then illuminating the substrate with an illumination beam having a frequency within the absorption band of the fluorescent substance so that fluorescent excitation takes place. The primary decay mechanisms of the excited states are radiative energy transfer, resonant energy transfer, and thermal decay, Hercules, *Fluorescence and Phosphorescence Analysis* (John Wiley & Sons, Inc., NY, 1966). At fixed intermolecular distances between the fluorescent molecules and absorber molecules, the relative amount of non-radiative decay by resonant energy transfer depends on the overlap between the absorption band of the absorber substance and the emission band of the fluorescent substance, which in turn depends on the physical and chemical parameters of the associated sample substance. As the degree of overlap between the absorption bands of the absorber substance and the emission bands of the fluorescent substance increase decay by resonant energy transfer increases, and as the overlap decreases decay by radiative energy transfer increases. Thus, the intensity of the detected fluorescent signal can be related to the physical and chemical parameters of the associated sample substance.

The present invention addresses problems associated with assay methods based on interactions between colorimetric indicators, or absorber substances, and fluorescent substances. It advantageously overcomes the problem of concentration dependent opacity of the absorber substance by immobilizing the substance on the surface of a suitable substrate. Problems due to the interaction of the sample substance with the fluorescent substance are overcome by immobilizing the fluorescent substance with respect to the substrate such that direct chemical contact between the fluorescent substance and the sample substance is minimized.

BRIEF DESCRIPTION OF THE DRAWINGS

Additional features and advantages of the invention will be apparent from the following descriptions of the preferred embodiments of the invention which are shown in the accompanying drawings, which are incorporated in and form a part of the specification. In the drawings.

DETAILED DESCRIPTION OF THE PREFERRED EMBODIMENTS

Figure 1:
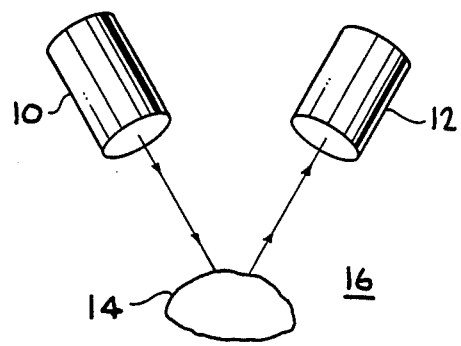
FIG. 1 diagrammatically illustrates a general optical configuration suitable for use with the present invention.

Reference will now be made in detail to the preferred embodiments of the invention, examples of which are illustrated in the accompanying drawings.

In accordance with present invention, apparatus and method are provided for monitoring physical and chemical parameters of an associated sample substance. A probe is provided which comprises a substrate material on or in which fluorescent substances and absorber substances are immobilized. The fluorescent substances and absorber substances are chosen such that the absorption bands of the absorber substances overlap the emission bands of the fluorescent substances. Moreover, the fluorescent substances and the absorber substances are immobilized on the substrate such that their intermolecular distances are close enough to render excited molecules of the fluorescent substances capable of decaying by resonant energy transfer to the absorber substances. Preferably the absorption characteristics of the absorber substances are responsive to the physical and chemical parameters of the associated sample substance, such that the degree of overlap between the emission bands of the fluorescent substance and the absorption bands of the absorber substance varies in response to changes in the physical and chemical parameters of the associated sample substance. Preferably the energy of the excited fluorescent states are not affected by the associated sample substance. In accordance with the invention the excited fluorescent molecules decay primarily by way of radiative energy transfer or by resonant energy transfer. Given a constant rate of production of excited fluorescent molecules, the ratio of radiative decay to resonance decay depends on the absorption characteristics of the absorber molecules. The greater the overlap between the emission band of the fluorescent molecules and the absorption band of the absorber molecules and the greater fluorescence efficiency of the fluorescent molecules, the more likely that decay will take place by resonant energy transfer. The less overlap and less fluorescent efficiency, the lower likelihood of decay by resonant energy transfer. Consequently, as the absorption characteristics of the absorber molecules change in response to changes in the physical and chemical parameters of the associated sample substance, more or less radiative decay of the excited fluorescent molecules is detected, thereby providing a measure of the change.

The absorber substance or the fluorescent substance may undergo chemical change in response to contact with the sample substance. Preferably, the chemical change is reversible.

An important feature of the present invention is the intermolecular distance between the fluorescent molecules and the absorber molecules. Resonant energy transfer can occur over distances of about 10–100 angstroms (Hercules, *Fluorescence and Phosphorescence*

*Analysis,* John Wiley & Sons, Inc., New York, 1966, pgs. 32-36). Absorber molecules must be within 10-100 angstroms of the fluorescent molecules for effective modulation of radiative decay, and preferably within about 10-70 angstroms. Preferably the substrate material has a high surface to volume ratio so that the number of fluorescent molecules illuminated per unit volume is maximized. Many diferent substrate materials and many different techniques for immobilizing fluorescent molecules and absorber molecules are available for use in accordance with the present invention. Such materials and techniques are well known in the arts of affinity chromatography and enzyme immobilization technology, e.g., Jacoby and Wilczek, editors, "Affinity Techniques," *Methods in Enzymology,* Vol. 34 (Academic Press, New York, 1974); Mosbach, editor, "Immobilized Enzymes," *Methods in Enzymology,* Vol. 44 (Academic Press, New York, 1976); and Maugh, II, Science, Vol. 223, pgs. 472-476 (Feb. 3, 1984). Among the possible substrate materials, inorganic substrate materials, such as controlled pore glass, sintered ceramic and sintered glass, are preferred. Inorganic support materials suitable for use in accordance with the present invention are described by Messing and Weetal, U.S. Pat. No. 3,519,538 issued July 7, 1970, entitled, "Chemically Coupled Enzymes," Weetal, U.S. Pat. No. 3,652,761 issued Mar. 28, 1972, entitled "Aminochemical Composites and Antigen or Antibody Purification Therewith," and Weetal, "Covalent Coupling Methods for Inorganic Support Materials," in *Methods of Enzymology,* Vol. 44, pgs. 134-148 (Academic Press, New York, 1976). Accordingly, these references are incorporated by reference for their descriptions of inorganic substrate materials and means for covalently coupling organic molecules thereto.

Glass can be employed as the substrate material in at least two ways. First, it can be used to immobilize both the fluorescent molecules and the absorber molecules either by adsorption or by covalent bonding or both. The preferred means of covalently bonding organic fluorescent molecules or absorber molecules to an inorganic support material such as glass is by way of a silane coupling substance. Silane coupling substances are silicon compounds which possess two different kinds of reactivity: organofunctional and silicon functional. That is silane coupling substances have a silicon portion with an affinity for inorganic materials such as glass or aluminum silicate, and they have an organic portion which may be tailored to combine with a variety of other organics, such as fluorescent molecules or absorber molecules. A glass particularly amenable to covalent bonding is controlled pore glass. It is commercially available in a variety of forms manufactured according the techniques of Hood et al., U.S. Pat. No. 2,106,764, Chapman et al., U.S. Pat. No. 3,485,687, and Haller, U.S. Pat. No. 3,549,524. Moreover, it is commercially available in a variety of pore sizes and with a variety of different silane coupling substances already attached (Pierce Chemical Company, *Handbook and General Catalog,* Rockford, Ill., 1983). Alternatively, silane coupling substances suitable for use with the present invention can be prepared and attached to control pore glass in accordance with the teachings of Weetal and Filbert, "Porous Glass for Affinity Chromotography Applications," *Methods of Enzymology,* Vol. 34, pgs. 59-72 (Academic Press, New York, 1974). Accordingly, this article is incorporated by reference.

Direct exposure of the fluorescent molecule to the associated sample substance can be avoided by manufacturing a control pore glass substrate such that it contains an inorganic fluorescent dopant such as a fluorescent lanthanide or fluorescent actinide.

A second way in which glass can be used as a substrate material is in the form of a sintered mass. The fluorescent molecules can be immobilized on the surface of the sintered glass by adsorption or by way of covalent bonds, for example, by means of silane coupling substances. The preferred method for immobilizing fluorescent molecules is to dope the glass with an inorganic species of fluorescent molecule. Materials suitable for such doping includes glasses and ceramics of the type developed for long term storage of high level radioactive waste products, e.g., phosphate glasses, borosilicate glasses, and ceramics such as SYN-ROC. Chapter 2, pgs. 4-34, *Characteristics of Solidified High-Level Waste Products,* Technical Report Series No. 187 (International Atomic Energy Agency, Vienna, 1979), is incorporated by reference for its description of glasses suitable for doping with lanthanides and actinides. Ringwood, U.S. Pat. No. 4,274,976, issued 23 June 1981; Aaron et al., U.S. Pat. No. 4,383,855, issued 17 May 1983; Beall et al., U.S. Pat. No. 4,314,909, issued 9 Feb. 1982; Ringwood and Cassin, "Immobilization of High Level Wastes in SYNROC Titanate Ceramic," in *Ceramics and Nuclear Waste Management,* Proceedings of an Internation Symposium held in Cincinnati, Ohio, Apr. 30 to May 2, 1979, Conf-790420, U.S. Department of Energy, pgs. 174-178, and Ringwood, et al. "Immobilization of High Level Nuclear Reactor Wastes in SYNROC," *Nature,* Vol. 278, pg. 219 (1979), are incorporated by reference for their description of the ceramic, SYNROC, or similar materials, which is suitable for use in accordance with the present invention.

Another source of substrate and fluorescent substances are colored filter glasses, which typically exhibit fluorescence, e.g., Weyl, *Colored Glasses,* chapter 24 (Society of Glass Technology, Sheffield, England, 1951); Bamford, *Colour Generation and Control in Glass,* section 3.3 (Elsevier Scientific Publishing Company, New York, 1977); and Turner, "Photoluminescence of Color Filter Glasses," *Applied Optics,* Vol. 12, pgs. 400-486 (1973), these references being incorporated by reference for their descriptions of fluorescent glasses. For example, uranium yellow filter glass (Corning 3-79) fluoresces strongly in the 525-550 nm range (green) when illuminated by light in the 375-500 nm range (UV to blue), and europium oxide doped soda-lime-silica glass fluoresces at wavelengths corresponding to orange-red.

Preferably, before or during the sintering process the surface of the glass or ceramic material is doped with an inorganic fluorescent substance. This can be accomplished by using ion implantation techniques, e.g., Mayer et al., *Ion Implantation in Semiconductors* (Academic Press, New York, 1970); Picraux and Peercy, "Ion Implantation of Surfaces," *Scientific American,* Vol. 252, pgs. 102-113 (1985); and Picraux and Pope, "Tailored Surface Modification by Ion Implantation and Laser Treatment," *Science,* vol. 226, pgs. 615-622 (1984). Surface doped substrates are superior to homogeneously doped substrates because the average intermolecular distances between absorber and fluorescent molecules are much less in the surface doped configuration. This makes it possible to attach absorber molecules within resonant energy transfer distance of practically all fluorescent molecules, unlike the case of the homogeneously doped substrate which always has fluorescent molecules deeply embedded in the interior of the substrate and outside the range for resonant energy transfer. Since the absorber molecules should be within 10-100 Angstroms of the fluorescer molecules, the fluorescent molecules, e.g. actinides or lanthanides, should be implanted within about 10-100 Angstroms from the glass surface on which the absorber is immobilized.

Once the absorber substance and fluorescent substance are attached to a suitable substrate material techniques for causing the fluorescent substance to fluoresce and for collecting and analyzing the resultant signal are well known in the art of fluorometry, e.g., Hercules, editor, Chapter 2, in *Fluorescence and Phosphorescence Analysis* (Interscience Publications, New York, 1966); White and Argauer, Chapter 2, in *Fluorescence Analysis* (Marcel Dekker, Inc., New York, 1970); and Parker, Chapter 3, in *Photoluminescence of Solutions* (Elsevier Publishing Co., New York, 1968). Accordingly, the respective chapters of these books are incorporated by reference.

FIG. 1 shows a general embodiment of the invention. Light source 10 illuminates substrate material 14, the material having the fluorescent substances and the absorber substances immobilized thereon. Substrate material 14 is in contact with sample substance 16, such that physical and chemical parameters of the sample substance can affect the absorption characteristics of the absorber substance. Changes in the absorption characteristics of the absorber substance modulates the fluorescent signal generated by the fluorescent substance. The modulated signal is detected by photometric detector 12.

Figure 2:
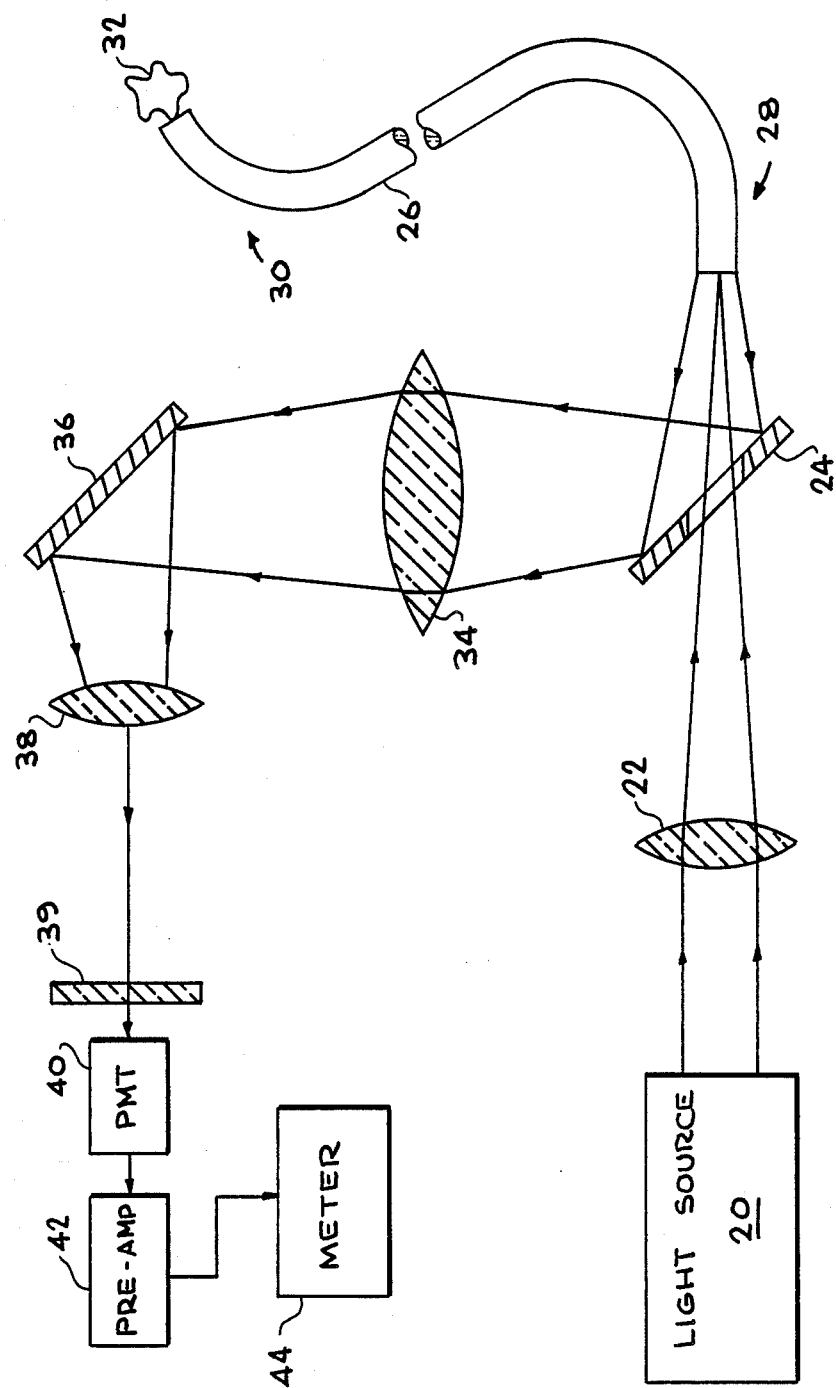
FIG. 2 diagrammatically illustrates an optical configuration employing a fiber optic suitable for use with the present preferred embodiment of the invention.

The preferred embodiment of the invention comprises substrate material attached to the end of a fiber optic. This embodiment is referred to as an "optrode." FIG. 2 diagrammatically illustrates an optical configuration suitable for use with the preferred embodiment. An illumination beam generated by light source 20 is focused by lens 22 and directed to first end 28 of fiber optic 26. Preferably light source 20 is a laser operating at a wavelength suitable for inducing the fluorescent substance to fluoresce, e.g., an argon ion laser operating at 488 nanometer for fluorescein. Most preferably, light source 20 is a mode locked laser generating pulses in the nanosecond range, or less. Pulsed output is preferable over continuous output because very high peak power can be achieved with relatively low average power thereby maximizing fluorescence output while minimizing the change of heat damage to system components, e.g., fiber optic 26, substrate material 32, and the means for attaching the substrate material to the fiber optic. The focal length of lens 22 is relatively long so that the angle of incidence of the illumination beam as it enters fiber optic 26 is within the acceptance angle of the fiber optic. This insures that all of the illumination beam will be transmitted by fiber optic 26. Fiber optic 26 preferably is a step index type communications fiber optic, such as a Valtec PC-10 (Valtec Corp., West Boylston, Mass.), or the like; although this is not a critical requirement of the invention, and other types of fiber optics can be used. Preferably, the substrate material 32 is in the form of a particle, referred to as a carrier particle, attached to second end 30 of fiber optic 26 by suitable attachment means, such as UV-cured expoxy, e.g., EPO-TEK 301, a trademarked adhesive of Epoxy Technology, Inc. (Billerica, MA), or the like. Preferably the average diameter of the substrate material or carrier particle 32 attached to the end of fiber optic 26 is at least the magnitude of the diameter of the core of fiber optic 26. Most preferably, the average diameter of the substrate material, or carrier particle, 32 is between about 1-3 times the diameter of the core of fiber optic 26.

The illumination beam exits fiber optic 26 at second end 30 so that the fluorescent substance on substrate material, or carrier particle, 32 is caused to fluoresce. A portion of the fluorescence is collected by fiber optic 26 at second end 30 and transmitted to first end 28. Adjacent to first end 28 apertured mirror 24 separates the "outgoing" illumination beam from the "incoming" signal. Lens 34 collects the fluorescent signal and focuses it on collimating lens 38 via mirror 36. The fluorescent signal passes through band pass filter 39 and is collected by photomultiplier tube 40. Band pass filter 39 is chosen to restrict the light incident on the photomultiplier tube 40 to that which has wavelengths corresponding to those of the fluorescent emission wavelength distribution of the fluorescent substance. For example, if the fluorescent substance is fluorescein and if light source 20 is an argon ion laser operating at 488 nanometer, band pass filter 39 can be chosen to pass light at wavelengths greater than 500 nanometers and less than 550 nanometers. Under these conditions scattered light from the illumination beam is prevented from reaching photomultipler tube 40. Output signal from the photomultiplier tube 40 is amplified by preamplifier 42. The output signal of preamplfer 42 can be read directly on meter 44, or the output signal can be manipulated further by a data processing means which provides a direct readout of the physical or chemical parameter of the sample substance being measured based on its relation to the intensity of the signal detected by photomultiplier tube 40.

Figure 3:
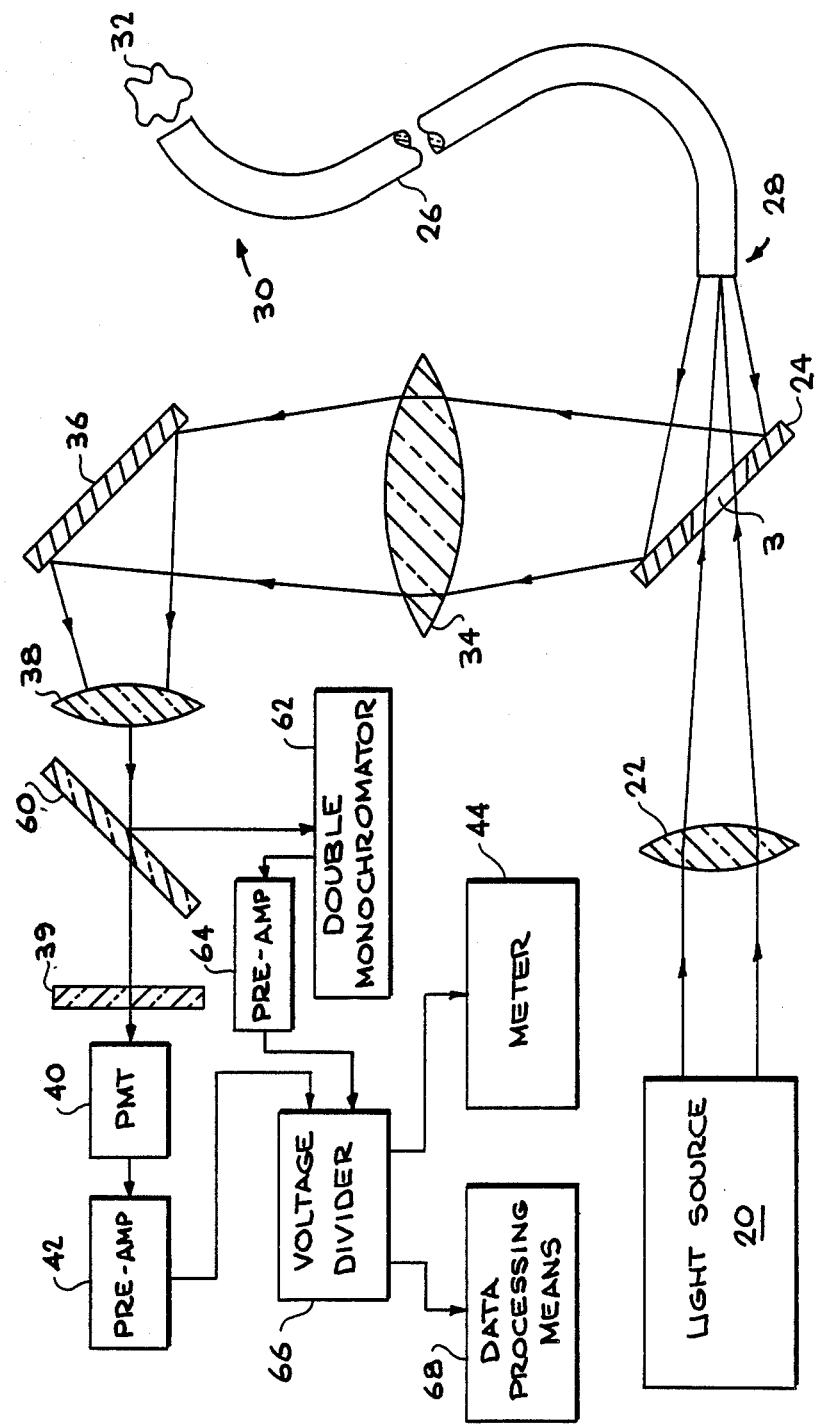
FIG. 3 diagrammatically illustrates an optical configuration suitable for use with the preferred embodiment which monitors Raman emissions backscattered from the fiber optic.

The accuracy of the determination of the physical and chemical parameters of the associated sample substance can be improved by providing means for monitoring the Raman emission from the fiber optic caused by the illumination-beam. In particular, the intensity of Raman emissions backscattered and transmitted to first end 28 can be monitored. The intensity of the backscattered Raman emissions depends directly on the intensity of the illumination beam and on the length of the fiber optic. By monitoring the ratio of the intensity of the fluorescent signal to the intensity of the collective Raman backscatter, errors due to fluctuations and illumination beam intensity are automatically factored out. That is, in an embodiment employing Raman backscatter measurement, a fluorescent signal—Raman backscattered intensity ratio is related to the physical and chemical parameter of the associated sample substance which is being measured. Techniques for measuring Raman backscatter are well known in the art of Raman spectroscopy, e.g., Chapter 2, entitled "Experimental Methods," in Tobin, *Laser Raman Spectroscopy* (Wiley-Interscience, New York, 1971) describes suitable apparatus. Accordingly, this chapter is incorporated by reference. FIG. 3 illustrates an optical configuration which includes means for monitoring Raman backscatter. Between beam collimating lens 38 and band pass filter 39 beam splitter 60 diverts a portion of the light collected by collection lens 34. The diverted portion is then directed to double monochromator 62 (e.g., model 1430, Spex Corp., Metuchen, N.J.), or like instrument, for measuring the intensity of the Raman backscatter.

Output from double monochromator 62 is preamplified by preamplifier 64 and received by analog voltage divider 66. Likewise output of preamplifier 42 is received by analog voltage divider 66. The output of analog voltage divider 66 is directly related to the fluorescence intensity-Raman backscatter intensity ratio, and can be read off of meter 44 or can be converted to a direct readout of the value of the physical or chemical parameter of interest by data processing means 68. The remaining components are as shown and described with reference to FIG. 2; aperture 3 is formed in mirror 24.

The following examples serve to illustrate the present invention. The concentration of reagents, temperatures, and values of other variable parameters are only to exemplify application of the present invention and are not to be considered as limitations thereof.

EXAMPLE I

Hydrogen Sulfide Detection

Figure 4:
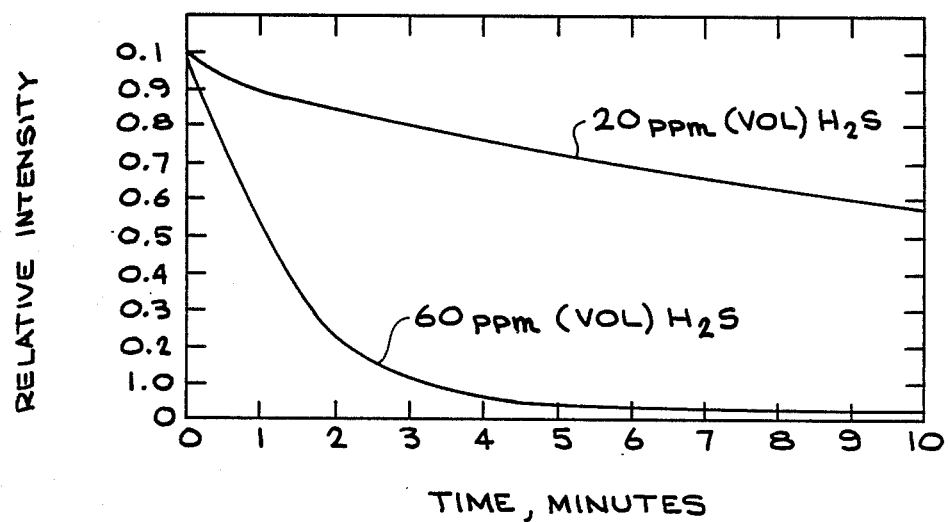
FIG. 4 illustrates curves which describe the response times and signal intensities generated by an embodiment for detecting hydrogen sulfide.

A Porous glass bead (Pierce Chemical Company, Rockford, IL) was attached to a fiber optic (Valtec Optical Group, Waltham, MA, model PC-10) by a UV-cured epoxy (Celanese Corp., Chatham, NJ). The attached bead was soaked for about 10 minutes in an aqueous solution of 1.0% lead acetate, 20.0% lithium nitrate, 0.1% EDTA, and 10 ppm fluorescein. The lithium nitrate is a hygroscopic substance used to reduce drying of the bead, and EDTA reduced lead complexing. The end of the fiber optic having the attached bead was placed in a flow chamber through which a carrier gas transported a known concentration of hydrogen sulfide. On the glass bead hydrogen sulfide reacts with lead acetate to form lead sulfide, a black absorber substance. FIG. 4 shows the response time and degree of signal reduction for carrier gases having 20 ppm and 60 ppm (by volume) hydrogen sulfide. In this example, the fluorescein was excited by 488 nm light from an argon ion laser operating at approximately 0.8 microwatts. The optical detection and excitation apparatus of FIG. 2 was employed. Acridine orange could be used as the fluorescent substance instead of fluorescein.

EXAMPLE II

Detection of Nitrogen Oxides

A porous, glass bead attached to a fiber optic (prepared in the same manner as in Example I) is soaked for 10 minutes in a solution comprising 100 ppm acridine orange in combination with reagents prepared according to Saltzman ("Colorimetric Microdetermination of Nitrogen Dioxide in the Atmosphere," *Anal. Chem.*, Vol. 26, pgs. 1949-1955 (1954)). The reagents consist of glacial acetic acid, sulfanilic acid, and N-(1-naphthyl)ethylenediamine dihydrochloride, prepared by dissolving about 5.0 grams of sulfanilic acid in approximately one liter of water containing 140.0 milliliter of glacial acetic acid. Next 20.0 milliliters of 0.1% solution of N-(1-naphthyl)-ethylenediamine dihydrochloride is added, and the mixture is diluted to 4.0 liters. Hereinafter this mixture will be referred to as the Saltzman reagent, or Saltzman's reagent. Nitrogen oxides and the Saltzman reagent combine to form an absorber substance which absorbs at approximately 548 nm (red). This absorbance band overlaps the acridine orange fluorescence emission band; thus resonant energy transfer reduces the intensity of the fluorescent signal. The fiber optic and bead were placed in a flow chamber, and a gas having about 20 ppm nitrogen dioxide was passed over the bead. The following table indicates the response time and relative reduction in fluorescence intensity:

| Time (Minutes) | Relative Intensity |
|---|---|
| 0 | 8.9 |
| 1 | 8.6 |
| 5 | 8.2 |
| 10 | 7.9 |
| 20 | 6.8 |
| 30 | 6.0 |
| 40 | 5.5 |

The acridine orange was excited at 488 nm by an argon ion laser operating at 0.26 microwatts.

EXAMPLE III pH Sensor

A sintered mass of uranium glass (Corning Glass Works, Corning NY, colored filter glass 3-79) is attached to the end of a fiber optic, as the porous glass of Examples I and II. The sintered mass is soaked for 30 minutes in a solution prepared as follows: 0.1 gram bromothymol blue is dissolved in 16.0 milliliters 0.01 N NaOH, then diluted to 250 milliliters. Bromothymol blue's absorption band ranges from about 540-640 nm for pH between about 6-8. This overlaps the emission band of the uranium glass which is between about 520-580 nm.

EXAMPLE IV

Detection of Alkali Metal Ions

Colorimetric detection of alkali metal ions by crown ethers is well known, e.g., Nakamura et al., "Photometric Reagents for Alkali Metal Ions Based on Crown Ether Complex formation," *Talanta*, Vol. 26, pgs. 921-927 (1979). Typically, the absorbance spectrum of the crown ether alkali metal complex shifts towards the red with respect to the non-complexed crown ether; thus, the intensity of the shifted spectra provides a quantitative measure of alkali metal ion concentration. The extent of the shift varies among different crown ether derivatives, e.g., Pacey et al., "Extraction of Potassium with Trifluoromethyl-substituted Chromogenic Crown Ethers," *Analyst*, Vol. 106, pgs. 636-640 (1981); and Pacey and Bubnis, "A New Chromogenic Crown Ether (4"-Cyano-2", 6"-Dinitro)-4'-Aminobenzo-15-Crown-5 as an Alkali Metal Extraction Reagent," *Analytical Letters*, Vol. 13, pgs. 1085-1091 (1980). And the order of preference for alkali ion complex formation for crown-6 and crown-5 ethers appears generally to be $K^+$ $Rb^+$ $Na^+$, although the strengths of the preferences vary amoung the different crown ethers (Nakamura et al., *Talanta*, Vol. 26, pgs. 921-927 (1979); and Pacey and Bubnis, *Analytical Letters*, Vol. 13, pgs. 1085-1091 (1980)).

In one embodiment of the present example fluorescein isothiocyanate (FITC) is attached to amino-derivatized controlled pore glass, e.g., aminoaryl, aminopropyl, or long chain alkylamine, available from Pierce Chemical Company (Rockford, IL) as product numbers 23415, 23909, and 24875, respectively, in the 1983 edition of Pierce's *Handbook and General Catalog*. Besides immobilizing the fluorescent and absorber substances, the amino-derivatived glass also provides a high pH environment (pH 10-11) necessary for the crown ethers to display chromogenic characteristics. Of course, the FITC must be exposed to the amino-derivatized glass in sufficiently low concentration that the amino groups are not saturated with fluorescein. The crown ethers are immobilized on the controlled pored glass by adsorption, or alternatively as described below or in accordance with Woo, U.S. Pat. No. 4,256,859, issued 17 Mar. 1981, entitled "Substituted Crown Ethers," this patent being incorporated by reference. Woo describes the synthesis of crown ether adducts which can be covalently attached to polymer supports.

It is believed that a major factor determining the binding preference of crown ethers to alkali metal ions is the closeness of fit between the ionic radius of the alkali metal ion and the size of the crown structure of the crown ether, e.g., Gokel, U.S. Pat. No. 4,436,664, entitled "Nitrogen Containing Polyether Macrocycles with a Sidearm Containing Neutral Electron Donor Groups," issued 13 Mar. 1984.

Accordingly, alkali metal ions are monitored in accordance with the invention by providing a plurality of separate sensors, at least one for each kind of alkali metal ion in the associated sample fluid, and each sensor having a chromogenic crown ether with a different binding preference for the ions present. By simultaneously comparing the response of each sensor to predetermined standards, the concentrations of each ion can be estimated (The simultaneous comparison at minimum involves solving a set of linear equations, and at most involves carrying out a least squares estimation). For example, in a physiological solution where only potassium and sodium are present, at least two sensors are provided whose crown ethers have different binding preferences for the alkali ions. Since potassium has a greater ionic radius than sodium, a series of sensors are preferred, each employing a different crown ether. For example, the crown ethers may have different sized crown structures, such as 18-crown-6 or 15-crown-5.

Crown ethers suitable for use with the present invention include 4'-(substituted-phenyl)-aminobenzo-18-crown-6, and -15-crown-5 ethers. Examples of these ethers are 4'-(4"-cyano-2", 6—-dinitrophenyl)-aminobenzo-15-crown-5 disclosed by Pacey and Bubnis, in *Analytical Letters,* Vol. 13, pgs, 1085-1091 (1980); 4'-picrylaminobenzo-15-crown-5 -disclosed by Nakamura et al., in *Talanta,* Vol. 26, pgs. 921-927 (1979); 4'-picrylaminobenzo-18-crown-6 disclosed by Nakamura et al., in *Analytical Chemistry,* Vol. 52, pgs. 1668-1671 (1980); 4'-(2", 6"-dinitro-4"-trifluoromethylphenyl) aminobenzo-15-crown-5 and 4'-(2", 4"-dinitro-6"-trifluoromethylphenyl)aminobenzo-15-crown-5 disclosed by Pacey et al., in U.S. Pat. No. 4,436,923 issued on 13 Mar. 1984; and derivatives thereof. Accordingly, the above references are incorporated by reference for their descriptions of how to prepare and use the above-mentioned crown ethers. Crown-7 and crown-4 ethers can also be used. The 4'-(substituted-phenyl)-amino-5'-substituted-benzo-18-crown-6 and 4'-(substituted phenyl)-amino-5'-substituted-benzo-15-crown-5 ethers can be used. The following ethers can be used:
4'-picrylamino-5'-nitrobenzo-18-crown-6,
4'-picrylamino-5'-nitrobenzo-15-crown-5,
4'-picrylamino-5'-bromo-18-crown-6,
4'-picrylamino-5'-bromo-15-crown 5,
4'-(2",6"-dinitro-4"-trifluoromethylphenyl)aminobenzo-18-crown-6,
4'-(2",4"-dinitro-6"-trifluoromethylphenyl)aminobenzo-18-crown-6,
4'-"-cyano-2",6"-dinitrophenyl)-aminobenzo-18-crown-6.

In accordance with this example, fiber optic sensors making up the said plurality are each prepared similarly to that described in Example I. That is, a porous glass substrate is attached to an end of a fiber optic so that the interface between the substrate and the fiber optic interferes minimally with light transmitted to and collected from the substrate by way of the fiber optic. As crown ethers are largely insoluable in aqueous solutions a hydrophobic substrate is provided, e.g., by appropriate silconization, such treatments and treated substrates being commercially available from Petrarch Systems, Inc. (Bristol, PA).

A. Hexadecanoyl fluorescein as the fluorescent substance and 4-picrylaminobenzo-18-crown-6 as the absorber: non-covalent attachment to the substrate.

A hydrophobic porous glass rod is attached to an end of a fiber optic. The attached rod is immersed in a solution comprising an organic solvent, hexadecanoyl fluorescein (available from Molecular Probes, Inc., Junction City, OR), at a concentration of about 100 ppm and 4-picrylaminobenzo-18-crown-6 at a concentration of about 100 ppm. The organic solvent preferably comprises a mixture of trichloromethane (i.e., chloroform), $CHCl_3$, and triethylamine, $(C_2H_5)_3N$, in proportions of about 50:1; or a mixture of trichloromethane and trioctylamine $(C_8H_{17})_3N$ in proportions of about 30:1; or a mixture of 1,1,2,2-tetrachloroethane $(CHCl_2)_2$ and trioctylamine in proportions of about 30:1. Most preferably, the organic solvent is mixture of 1,1,2,2-tetrachloroethane and trioctylamine in a ratio of about 30:1. The optrode is ready for use after removal from the solution.

B. Fluorescein as the fluorescent substance and 4-picrylaminobenzo-18-crown-6 as absorber: covalent attachment.

An amino-derivatized porous glass rod is attached to an end of a fiber optic. The attached porous glass rod is immersed in a cumene (isopropylbenzene) solution containing 4-picrylaminobenzo-18-crown-6 at a concentration of about 100 ppm, and FITC at a concentration of about 100 ppm. After immersion the rod is washed in cumene and dried.

The descriptions of the foregoing examples of the invention have been presented for purposes of illustration and description. They are not intended to be exhaustive or to limit the invention to the precise form disclosedd, and obviously many modifications and variations are possible in light of the above teaching. The examples were chosen and described in order to best explain the principles of the invention and its practical application to thereby enable others skilled in the art to best utilize the invention in various contexts and with various modifications as are suited to the particular use contemplated. It is intended that the scope of the invention be defined by the claims appended hereto.

I claim:

1. A method for monitoring physical and chemical parameters of a sample substance and for generating a signal related to said physical and chemical parameters, the method comprising the steps of:
   immobilizing on a substrate, a fluorescent substance having an emission band and an absorption band;
   immobilizing on the same substrate, an absorber substance having an absorption band overlapping the emission band of the fluorescent substance, the degree of overlap being responsive to the physical and chemical parameters of the sample substance, and the absorber substance being immobilized such that an effective number of molecules of the absorber substance are closely adjacent to an effective number of molecules of the fluorescent substance to produce detectable resonant energy transfer therebetween;

contacting the substrate with the sample substance;

illuminating the fluorescent substance with an illumination beam having a frequency within the absorption band of the fluorescent substance, so that excited fluorescent states are generated in the fluorescent substance;

detecting a signal resulting from the decay of the excited fluorescent states;

providing a fiber optic through which said illumination beam is transmitted from a first end of the fiber optic to a second end of the fiber optic;

attaching said substrate to the second end of the fiber optic such that light from said illumination beam emanating from the second end of the fiber optic illuminates said fluorescent substance and such that said resulting signal is collected by the second end of the fiber optic and transmitted to the first end of the fiber optic;

separating at the first end of the fiber optic said illumination beam from said resulting signal;

measuring the intensity of backscattered Raman emissions from the fiber;

forming a ratio of the resulting signal to the backscattered Raman intensity;

extracting information concerning the physical and chemical parameters of the sample substance from the ratio.

2. The method of claim 1 wherein said effective number of molecules of said absorber substance are within about 10–100 Angstroms of said effective number of molecules of said fluorescent substance.

3. The method of claim 2 wherein said effective number of molecules of said absorber substance are within about 10–70 Angstroms of said effective number of molecules of said fluorescent substance.

4. The method of claim 1 wherein said substrate is porous glass.

5. The method of claim 4 wherein said effective number of molecules of said absorber substance are within about 10–70 Angstroms of said effective number of molecules of said fluorescent substance.

6. The method of claim 1 wherein said substrate is sintered glass.

7. The method of claim 6 wherein said effective number of molecules of said absorber substance are within about 10–70 Angstroms of said effective number of molecules of said fluorescent substance.

8. An apparatus for monitoring physical and chemical parameters of a sample substance and for generating an optical signal related to said physical and chemical parameters, the apparatus comprising:

a fluorescent substance having an absorption band and an emission band;

an absorber substance having an absorption band overlapping the emission band of the fluorescent substance, the degree of overlap being responsive to the physical and chemical parameters of the sample substance;

a substrate on which the fluorescent substance and the absorber substance are immobilized such that an effective number of molecules of the absorber substance are closely adjacent to an effective number of molecules of the fluorescent substance to produce detectable resonant energy transfer therebetween;

means for illuminating the fluorescent substance with light having a wavelength within the absorption band of the fluorescent substance so that excited fluorescent states are generated wherein said means for illuminating includes a fiber optic through which an illumination beam from an associated light source is transmitted from a first end of the fiber optic to a second end of the fiber optic, the fiber optic having a core, and wherein said substrate is attached to the second end of the fiber optic such that light from the illumination beam emanating from the second end of the fiber optic illuminates said fluorescent substance, and such that said resulting optical signal is collected by the second end of the fiber optic and transmitted to the first end of the fiber optic, and wherein said means for illuminating further includes separation means adjacent to the first end of the fiber optic for separating the illuminating beam from said resulting optical signal;

means for detecting an optical signal resulting from the decay of the excited fluorescent states;

means for measuring the intensity of backscattered Raman emissions from the fiber; and means for forming a ratio of the optical signal to the backscattered Raman intensity.

9. The apparatus of claim 8 wherein said effective number of molecules of said absorber substance are within about 10–100 Angstroms of said effective number of molecules of said fluorescent substance.

10. The apparatus of claim 8 wherein said means for detecting an optical signal comprises means for detecting fluorescent emissions of said fluorescent substance modulated by said absorber substance.

11. The apparatus of claim 10 wherein said effective number of molecules of said absorber substance are within about 10–70 Angstroms of said effective number of molecules of said fluorescent substance.

12. The apparatus of claim 11 wherein said substrate is in the form of a carrier particle.

13. The apparatus of claim 12 wherein said fiber optic core has a diameter and said carrier particle has an average diameter between about 1–3 times the diameter of said core of said fiber optic.

14. The apparatus of claim 13 wherein said carrier particle is made of porous glass.

15. The apparatus of claim 14 wherein said porous glass is doped with said fluorescent substance which is selected from the group consisting of ions of fluorescent lanthanides or fluoresscent actinides.

16. The apparatus of claim 13 wherein said carrier particle is made of sintered glass.

17. The apparatus of claim 16 wherein said sintered glass is doped with said fluorescent substance which is selected from the group consisting of ions of fluorescent lanthanides or fluorescent actinides.

18. The apparatus of claim 17 wherein said sintered glass is doped with said ions of fluorescent lanthanides or fluorescent actinides by ion implantation so that the implanted ions of fluorescent lanthanides or fluorescent actinides are within about 10–100 Angstroms from the surface of the glass.

19. The apparatus of claim 17 wherein said doped sintered glass is uranium glass.

20. A method for detecting nitrogen oxides in a sample fluid, the method comprising the steps of:
providing a fiber optic through which an illumination beam from an associated light source is transmitted from a first end of the fiber optic to a second end of the fiber optic, and a carrier particle attached to the second end of the fiber optic such that light from the illumination beam emanating from the second end of the fiber optic illuminates the carrier particle;
immobilizing on the carrier particle Saltzman's reagent, the Saltzman's reagent reacting with any nitrogen oxides in the sample fluid when in contact therewith to produce an absorber substance on the particle, the absorber substance having an absorption band;
immobilizing on the carrier particle a fluorescent substance having an emission band overlapping the absorption band of any absorber substance formed, such that an effective number of molecules of the fluorescent substance are closely adjacent to an effective number of molecules of the absorber to produce detectable resonant energy transfer therebetween whenever the Saltzman's reagent reacts with nitrogen oxides in the sample fluid;
contacting the carrier particle with the sample fluid;
illuminating the fluorescent substance with the illumination beam so that excited fluorescent states are generated in the fluorescent substance;
collecting at the second end of the fiber optic fluorescent emissions of the fluorescent substance;
separating at the first end of the fiber optic the collected fluorescent emissions from the illumination beam;
measuring the intensity of backscattered Raman emissions from the fiber;
forming a ratio of the fluorescent emissions to the backscattered Raman intensity; and
relating the ratio to the concentration of nitrogen oxides in the sample fluid.

21. A method for detecting hydrogen sulfide in a sample fluid, the method comprising the steps of:
providing a fiber optic through which an illumination beam from an associated light source is transmitted from a first end of the fiber optic to a second end of the fiber optic, and a carrier particle attached to the second end of the fiber optic such that light from the illumination beam emanating from the second end of the fiber optic illuminates the carrier particle;
immobilizing on the carrier particle lead acetate, the lead acetate reacting with any hydrogen sulfide in the sample fluid when in contact therewith to produce lead sulfide having an absorption band;
immobilizing on the carrier particle a fluorescent substance having an emission band overlapping the absorption band of any lead sulfide formed, such that an effective number of molecules are the fluorescent substance are closely adjacent to an effective number of lead sulfide molecules to produce detectable resonant energy transfer therebetween whenever the lead acetate reacts with hydrogen sulfide in the sample fluid;
contacting the carrier particle with the sample fluid;
illuminating the fluorescent substance with the illumination beam so that excited fluorescent states are generated in the fluorescent substance;
collecting at the second end of the fiber optic fluorescent emissions of the fluorescent substance;
separating at the first end of the fiber optic the collected fluorescent emissions from the illumination beam;
measuring the intensity of backscattered Raman emissions from the fiber;
forming a ratio of the fluorescent emissions to the backscattered Raman intensity; and
relating the ratio to the concentration of hydrogen sulfide in the sample fluid.

22. The method of claim 21 wherein said fluorescent substance is fluorescein.

23. The method of claim 21 wherein said fluorescent substance is acridine orange.

24. A method for detecting alkali metal ions in a sample fluid, the method comprising the steps of:
providing a fiber optic through which an illumination beam from an associated light source is transmitted from a first end of the fiber optic to a second end of the fiber optic;
providing a carrier particle attached to the second end of the fiber optic such that light from the illumination beam emanating from the second end of the fiber optic illuminates the carrier particle;
immobilizing on the carrier particle a chromogenic crown ether, the chromogenic crown ether interacting with any alkali metal ions in the sample fluid when in contact therewith to produce a crown ether-alkali metal ion complex having an absorption band;
immobilizing on the carrier particle a fluorescent substance having an emission band overlapping the absorption band of any crown ether-alkali metal ion complex formed, such that an effective number of molecules of the fluorescent substance are closely adjacent to an effective number of crown ether-alkali metal ion complex molecules to produce detectable resonant energy transfer therebetween whenever such complex molecules are formed;
contacting the carrier particle with the sample fluid wherein the contacting step is carried out at a pH sufficient for the crown ether to display chromogenic characteristics in the presence of alkali metal ions;
illuminating the fluorescent substance with the illumination beam so that excited fluorescent states are generated in the fluorescent substance;
collecting at the second end of the fiber optic fluorescent emissions of the fluorescent substance;
separating at the first end of the fiber optic the collected fluorescent emissions from the illumination beam; and
relating the intensity of the collected and separated fluorescent emissions to the concentration of alkali metal ions in the sample fluid.

25. The method of claim 24 wherein said chromogenic crown ether is selected from the group consisting of crown-7, crown-6, crown-5, or crown-4 ethers.

26. The method of claim 25 wherein said chromogenic crown ether is selected from the group consisting of crown-6 or crown-5 ethers.

27. The method of claim 26 wherein said crown-6 and crown-5 ethers are 18-crown-6 and 15-crown-5 ethers, respectively.

28. The method of claim 27 wherein said alkali metal ions are potassium and/or sodium.

29. The method of claim 28 wherein said fluorescent substance is fluorescein.

30. The method of claim 27 wherein said 18-crown-6 and 15-crown-5 ethers are 4'-(substituted-phenyl)-amino-5'-substituted-benzo-18-crown-6 and 4'-(substituted-phenyl)-amino-5'-substituted-benzo-15-crown-5 ethers, respectively.

31. The method of claim 30 wherein said 18-crown-6 and 15-crown-5 ethers are 4'-(substituted-phenyl)-aminobenzo-18-crown-6 and 4'-(substituted-phenyl)-aminobenzo-15-crown-5 ethers, respectively.

32. The method of claim 31 wherein said 18-crown-6 and 15-crown-5 ethers are selected from the group consisting of
4'-picrylaminobenzo-18-crown-6,
4'-picrylaminobenzo-15-crown-5,
4'-picrylamino-5'-nitrobenzo-18-crown-6,
4'-picrylamino-5'-nitrobenzo-15-crown-5,
4'-picrylamino-5'-bromo-18-crown-6,
4'-picrylamino-5'-bromo-15-crown 5,
4'-(2'',6''-dinitro-4''-trifluoromethylphenyl)aminobenzo-18-crown-6
4'-(2'',6''-dinitro-4''-trifluoromethylphenyl)aminobenzo-15crown-5,
4'-(2'',4''-dinitro-6''-trifluoromethylphenyl)aminobenzo-18-crown-6,
4'-(2'',4''-dinitro-6''-trifluoromethylphenyl)aminobenzo-15-crown-5,
4'-(4''-cyano-2'',6''-dinitrophenyl)-aminobenzo-18-crown-6, and
4'-(4''-cyano-2'',6''-dinitrophenyl)-aminobenzo-15-crown-5.

33. The method of claim 32 wherein said 18-crown-6 and 15-crown-5 ethers are selected from the group consisting of:
4'-picrylaminobenzo-18-crown-6,
4'-picrylaminobenzo-15-crown-5,
4'-(2'',6''-dinitro-4''-trifluoromethylphenyl)aminobenzo-15-crown-5,
4'-(2''4''-dinitro-6''-trifluoremethylphenyl)aminobenzo-15-crown-5, and
4'-(4''-cyano-2'',6''-dinitrophenyl)-aminobenzo-15-crown-5.

34. The method of claim 33 wherein said 18-crown-6 and 15-crown-5 ethers are respectively 4'-picrylaminobenzo-18-crown-6 and 4'-picrylaminobenzo-15-crown-5.

35. An apparatus for monitoring alkali metal ions in a sample substance, the apparatus comprising:
a fiber optic through which an illumination beam from an associated light source is transmitted from a first end of the fiber optic to a second end of the fiber optic;
a carrier particle attached to the second end of the fiber optic such that light from the illumination beam emanating from the second end of the fiber optic illuminates the carrier particle;
a fluorescent substance immobilized on the carrier particle, the fluorescent substance having an emission band; and
a chromogenic crown ether immobilized on the carrier particle, the chromogenic crown ether having a first absorption band, and the chromogenic crown ether being capable of forming a crown ether-alkali metal ion complex having a second absorption band, and the first absorption band and the second absorption band overlapping the emission band of the fluorescent substance to different degrees;
means for detecting a signal from the fluorescent substance modulated by the ether-alkali metal complex.

36. The apparatus of claim 35 wherein said chromogenic crown ether is selected from the group consisting of 18-crown-6 and 15-crown-5 ethers.

37. The apparatus of claim 36 wherein said carrier particle is porous glass.

38. The apparatus of claim 37 wherein said fluorescent substance is fluorescein.

39. The apparatus of claim 36 wherein said 18-crown-6 and 15-crown-5 ethers are respectively 4'-picrylaminobenzo-18-crown-6 and 4'-picrylaminobenzo-15-crown-5.

* * * * *